US010810756B2

United States Patent
Martínez-Enríquez et al.

(10) Patent No.: US 10,810,756 B2
(45) Date of Patent: Oct. 20, 2020

(54) METHOD OF ESTIMATING A FULL SHAPE OF THE CRYSTALLINE LENS FROM MEASUREMENTS TAKEN BY OPTIC IMAGING TECHNIQUES AND METHOD OF ESTIMATING AN INTRAOCULAR LENS POSITION IN A CATARACT SURGERY

(71) Applicant: CONSEJO SUPERIOR DE INVESTIGACIONES CIENTÍFICAS, Madrid (ES)

(72) Inventors: Eduardo Martínez-Enríquez, Madrid (ES); Susana Marcos-Celestino, Madrid (ES); Carlos Dorronsoro-Díaz, Madrid (ES)

(73) Assignee: CONSEJO SUPERIOR DE INVESTIGACIONES CIENTIFICAS, Madrid (ES)

( * ) Notice: Subject to any disclaimer, the term of this patent is extended or adjusted under 35 U.S.C. 154(b) by 25 days.

(21) Appl. No.: 15/583,441

(22) Filed: May 1, 2017

(65) Prior Publication Data

US 2017/0316571 A1 Nov. 2, 2017

Related U.S. Application Data

(60) Provisional application No. 62/329,392, filed on Apr. 29, 2016.

(51) Int. Cl.
*G06T 7/62* (2017.01)
*A61B 3/10* (2006.01)
(Continued)

(52) U.S. Cl.
CPC .............. *G06T 7/62* (2017.01); *A61B 3/0025* (2013.01); *A61B 3/102* (2013.01); *A61B 3/1173* (2013.01);
(Continued)

(58) Field of Classification Search
CPC ..... A61B 3/0025; A61B 3/102; A61B 3/1173; G06T 7/50; G06T 7/62; G06T 7/70; G06T 2207/10101; G06T 2207/30041
See application file for complete search history.

(56) References Cited

U.S. PATENT DOCUMENTS

| 8,321,184 | B1* | 11/2012 | Urs | A61F 2/1613 |
| | | | | 703/2 |
| 2010/0121612 | A1* | 5/2010 | Ho | A61B 3/1173 |
| | | | | 703/1 |
| 2017/0079526 | A1* | 3/2017 | Tamura | A61B 3/09 |

FOREIGN PATENT DOCUMENTS

WO 2011/026068 A2 3/2011

OTHER PUBLICATIONS

Borja et al. "Distortions of the posterior surface in optical coherence tomography images of the isolated crystalline lens: effect of the lens index gradient." Biomedical optics express 1.5 (2010): 1331-1340.*

(Continued)

*Primary Examiner* — Katrina R Fujita

(57) ABSTRACT

The present invention relates to a method and a device for estimating a full shape of a lens of an eye from measurements of the lens taken in-vivo by optical imaging techniques, the measurements comprising visible portions of the lens, the method comprises defining non-visible portions of the lens parting from the in-vivo measurements and using a geometrical model of a lens previously built from ex-vivo measurements.

The full shape parameters of the crystalline lens can be estimated in the present invention from optical imaging techniques to improve the estimation of the IOL position and thus the IOL power selection.

19 Claims, 9 Drawing Sheets

(51) Int. Cl.
  *A61B 3/00*    (2006.01)
  *A61B 3/117*    (2006.01)
  *G06T 7/50*    (2017.01)
  *G06T 7/70*    (2017.01)

(52) U.S. Cl.
  CPC ............... *G06T 7/50* (2017.01); *G06T 7/70* (2017.01); *G06T 2207/10101* (2013.01); *G06T 2207/30041* (2013.01)

(56) References Cited

OTHER PUBLICATIONS

Hermans et al. "Constant volume of the human lens and decrease in surface area of the capsular bag during accommodation: an MRI and Scheimpflug study." Investigative ophthalmology & visual science 50.1 (2009): 281-289.*

Ortiz et al. "Optical distortion correction in optical coherence tomography for quantitative ocular anterior segment by three-dimensional imaging." Optics express 18.3 (2010): 2782-2796.*

Smith et al. "Mathematical models for describing the shape of the in vitro unstretched human crystalline lens." Vision research 49.20 (2009): 2442-2452.*

Navarro, Rafael, Fernando Palos, and Luis González. "Adaptive model of the gradient index of the human lens. I. Formulation and model of aging ex vivo lenses." JOSA A 24.8 (2007): 2175-2185. (Year: 2007).*

Navarro, Rafael, Fernando Palos, and Luís M. González. "Adaptive model of the gradient index of the human lens. II. Optics of the accommodating aging lens." JOSA A 24.9 (2007): 2911-2920. (Year: 2007).*

Siedlecki et al. "Distortion correction of OCT images of the crystalline lens: GRIN approach." Optometry and Vision Science 89.5 ( 2012): E709. (Year: 2012).*

Siedleckiet al. "Schematic eye with a gradient-index lens and aspheric surfaces." Optics letters 29.11 (2004): 1197-1199. (Year: 2004).*

I. Grulkowski, et al.; "*Anterior segment imaging with Spectral OCT system using a high-speed CMOS camera*"; Optics Express, vol. 17, No. 6; Mar. 16, 2009; pp. 4842-4858 (17 pages).

T. Olsen, MD, PhD, et al.; "*C constant: New concept for ray tracing-assisted intraocular lens power calculation*"; Journal of Cataract & Refractive Surgery, vol. 40; May 2014; pp. 764-773 (10 pages).

Thomas Olsen; "*Calculation of intraocular lens power: a review*"; Acta Ophthalmologican Scandinavica, vol. 85; 2007; pp. 472-485 (14 pages).

J. Birkenfeld; "*Contribution of Shape and Gradient Refractive Index to the Spherical Aberration of Isolated Human Lenses*"; IVOS—Association for Research in Vision and Ophthalmology Journal, vol. 55, No. 4; Apr. 2014; pp. 2599-2607 (9 pages).

J. Retzlaff, MD, et al.; "*Development of the SRK/T intraocular lens implant power calculation formula*"; Journal of Cataract & Refractive Surgery, vol. 16, Issue 3; May 1990; pp. 333-3340 (8 pages).

P. Perez-Merino et al; "*OCT-based crystalline lens topography in accommodating eyes*"; Biomedical Optics Express, vol. 6, No. 12; Dec. 2015; pp. 5039-5054 (16 pages).

Thomas Olsen, MD; "*Prediction of the effective postoperative (intraocular lens) anterior chamber depth*"; Journal of Cataract & Refractive Surgery, vol. 32; Mar. 3006; pp. 419-424 (6 pages).

S. Uhlhorn et al.; "*Refractive Index Measurement of the Isolated Crystalline Lens Using Optical Coherence Tomography*"; Vision Research, vol. 48, Issue 27; Dec. 2008; pp. 2732-2738 (19 pages).

Sverker Norrby, PhD; "*Sources of error in intraocular lens power calculation*"; Journal of Cataract & Refractive Surgery, vol. 34, Issue 3; Mar. 2008; pp. 368-376 (9 pages).

\* cited by examiner

METHOD OF ESTIMATING A FULL SHAPE OF THE CRYSTALLINE LENS FROM MEASUREMENTS TAKEN BY OPTIC IMAGING TECHNIQUES AND METHOD OF ESTIMATING AN INTRAOCULAR LENS POSITION IN A CATARACT SURGERY

TECHNICAL FIELD

The present invention is encompassed within the ophthalmic field and more specifically, it relates to providing precise geometric measurements of the crystalline lens and accurate estimations of the intraocular lens position in a cataract surgery.

STATE OF THE ART

The main optical elements of the eye are the crystalline lens and the cornea. The crystalline lens is the responsible for the focusing ability of the eye (accommodation). Therefore, it is important to understand the properties of the crystalline lens for the design and evaluation of solutions for presbyopia and for cataracts.

There are many studies relating to the geometry of the human crystalline lens, both ex-vivo and in-vivo.

In-vivo measurements of the crystalline lens are typically obtained using Purkinje imaging or Scheimpflug imaging, Magnetic Resonance Imaging (MRI) and Optical Coherence Tomography (OCT). These measurements include lens radii of curvature, lens tilt and decentration, lens internal structure and surface topography and their changes with age and accommodation.

However optical imaging methods only allow to retrieve information visible through the pupil, thereby preventing direct estimation of some important parameters such as the equatorial plane position, EPP, the volume, VOL, the surface area, SA, or the diameter of the lens at the equatorial plane, DIA.

A scarce number of studies have reported in-vivo the shape of the entire lens and associated interesting parameters such as EPP, VOL, SA or DIA. Most of these reports are based on MRI of the lens, which is able to capture non-distorted images of the entire lens. However, MRI-based techniques have significantly lower resolution (around 20-30 times less) and much higher acquisition times than optical imaging techniques, which makes them not viable for obtaining parameters with the required precision.

Previous approaches to estimate lens geometrical parameters such as VOL, EPP, SA and DIA from optical imaging techniques estimate such parameters by intersecting two parametric surfaces that best fit the available data within the pupil size (PS) of the anterior (AL) and the posterior (PL) surfaces of the lens. However, these methods (in the following referred to as 'intersection approaches') result in an overestimation of the parameters VOL, SA and DIA, and an underestimation the EPP (anterior shift).

Other approaches consider a constant value for the EPP (relative to the lens thickness), although some reports suggest that EPP is subject-dependent.

Patent document WO-A2-2011/026068 discloses a method for creating a geometric model of an ocular lens capsule using the radii of curvature of the anterior and the posterior lens surfaces and the lens thickness previously determined by Scheimpflug imaging. Being an intersection approach, it is subject to the problems explained above.

Also, patent document US-A-2010/121612 discloses a method for characterizing an entire lens surface including anterior and posterior hemispheres as well as the equatorial region as a single continuous mathematical representation. The method disclosed is based on shadow photogrammetry of eye tissues which provides the full lens contour. It is only valid ex-vivo.

Therefore, there is a need for a method which provides an estimation of the full geometry or shape of the crystalline lens, especially in-vivo, and/or of the capsular bag and at the same time reduces the estimation error with respect to known methods.

Preoperative estimation of postoperative IOL position (ELP) is the largest contribution of error to the modern IOL power calculation (*"Sources of error in intraocular lens power calculation"* Norrby S., Journal of Cataract & Refractive Surgery 2008; 34:368-376). Therefore, any improvement in postoperative IOL position prediction will provide better IOL power selection and thus refractive and visual outcomes using typical formulas or ray tracing-assisted IOL power calculation.

Different preoperative variables have been used in the design of formulas for the prediction of post-operative IOL position, so-called estimated lens position (ELP). For example, the widely used SRK/T formula (*"Development of the SRK/T intraocular lens implant power calculation formula"*, Retzlaff J. A., Sanders D, Kraff M, Journal of Cataract & Refractive Surgery 1990; 16:333-340) uses the axial length and anterior corneal quantification to predict the IOL position; the Haigis formula (*"The Haigis formula"*, Haigis W, In: Shammas H J (ed). Intraocular lens power calculations. Thorofare, N.J.: Slack Inc. 2004; 5-57) uses the axial length and preoperative ACD; or the Olsen formula (*"Prediction of the effective postoperative (intraocular lens) anterior chamber depth"*, Olsen T, Journal of Cataract & Refractive Surgery 2006; 32:419-424), which employs a 5-variable model, in which the input parameters are the axial length, the preoperative ACD, the lens thickness, the average corneal radius and the preoperative refraction. A comprehensive review can be found in (*"Calculation of intraocular lens power: a review"*, Olsen T, Acta Ophtalmologica 2007; 85:472-485, Table 5). In most approaches, ELP is estimated from parameters unrelated with the shape of the crystalline lens. Reported approaches using some information on the crystalline lens use axial measurements (1-dimensional) or 2-dimensional models/measurements that never includes the full shape of the crystalline lens, with intuitively seems critical to accurately estimates the postoperative IOL position (as the IOL will be placed inside the capsular bag of the crystalline lens).

DESCRIPTION OF THE INVENTION

In the present invention, a method for estimating a shape of a lens of an eye is provided, which shape is estimated using measurements taken by optical imaging techniques, such as Optical Coherence Tomography (OCT). Also, a method for estimating the ELP from the preoperative shape of the lens is provided.

In the present invention, we use 3-D full shape parameters of the crystalline lens estimated from optical imaging techniques to improve the estimation of the IOL position and thus the IOL power selection.

A first aspect of the invention relates to a method of estimating a full shape of a lens of an eye from measurements of the lens taken in-vivo by optical imaging techniques, the measurements comprising visible portions of the lens, the method comprises defining non-visible portions of the lens parting from the in-vivo measurements and using a geometrical model of a lens previously built from ex-vivo measurements; the geometrical model is a model that describes the geometry of the lens, usually as a function of a set of parameters. That is, the method comprises defining non-visible portions of the lens using the in-vivo measurements to an extent given by a geometrical model previously defined and validated with ex-vivo measurements. With the ex-vivo measurements different parameters of the geometrical model can be trained, and also the model can be validated.

In some embodiments, the method preferably comprises fitting the in-vivo measurements to a first parametric surface corresponding to an anterior surface, AL, of the lens and to a second parametric surface corresponding to a posterior surface, PL, of the lens. And then, defining the non-visible portions of the lens comprises:

extrapolating the first and second parametric surfaces to an extent given by a first parameter $\alpha$ to define a central region of the lens, the central region including the visible portions of the lens and an extrapolated non-visible region;

using data from a part of the central region of the lens to define an equatorial region of the lens (with at least a third parametric surface), the part of the central region being given by a second parameter $\rho$;

the first and second parameters $\alpha$, $\rho$ are provided by the geometrical model built from the ex-vivo measurements.

That is, in order to estimate the non-visible portions of the lens:

firstly, the first and second parametric surfaces are extrapolated to the extent given by $\alpha$ to define the central region of the lens; and then data within a part $\rho$ of that central region obtained in the previous step are used to obtain at least a third parametric surface that defines the equatorial region of the lens.

The data used in the last step can be the whole central region (defined by surfaces $z_{ext}*(AL)$, $z_{ext}*(PL)$) within the part $\rho$, or it is possible to just use a few selected points of the extrapolated surfaces within the part $\rho$.

It is then possible to obtain the at least third parametric surface by fitting with a surface the central region of the lens within the part $\rho$ (obtain the at least third parametric surface that better describes the data of the central region of the lens within the part $\rho$). It is also possible to use the data from the part $\rho$ to impose continuity and differentiability conditions between the extrapolated first and second parametric surfaces and the at least third parametric surface.

Another aspect of the invention relates to a method of estimating a full shape of a lens of an eye from measurements taken by optical imaging techniques of the lens, the method comprises:

fitting the measurements to a first parametric surface corresponding to an anterior surface, AL, of the lens and to a second parametric surface corresponding to a posterior surface, PL, of the lens;

extrapolating the first and second parametric surfaces to an extent given by a first parameter $\alpha$ to define a central region of the lens;

using data from a part of the central region of the lens to define an equatorial region of the lens by obtaining at least a third parametric surface that adapts to such data, the part being given by a second parameter $\rho$.

In some embodiments, the step of using data from the part of the central region of the lens may comprise fitting such data to the at least third parametric surface.

In other embodiments, the step of using data from the part of the central region of the lens comprises imposing continuity and differentiability conditions between the extrapolated first and second parametric surfaces and the at least third parametric surface. While these conditions are more restrictive and remove degrees of freedom from the model, they can be really useful in ray tracing applications or when a mathematical model of the full shape of the lens is required.

In this case, the measurements of the lens taken by optical imaging techniques can be taken in-vivo (preferably in a human eye) and, therefore, just relate to respective portions of the anterior and the posterior surfaces of the lens visible through a portion of the eye (the visible pupil size, PS). These in-vivo measurements are thus key to optimize performance of state-of-the-art cataract surgery, because they will allow to construct patient-specific models in order to predict the best IOL to be implanted in a given patient.

In the present text, by parametric surface it is meant any function evaluable at any point of an extended domain, or a closed-form mathematical expression.

In preferred embodiments, the extent $\alpha$ to which the first and second parametric surfaces are extrapolated to define the central region of the lens is made dependent on the lens geometry, in more particularly, on an intersection diameter of the lens, ID, which can be obtained from the visible portions within the pupil for every lens. Preferably $\alpha$ is chosen as a proportion of the intersection diameter ID of the lens.

Preferably, $\alpha$ is equal to between 0.55 and 0.95 times the intersection diameter ID of the lens, and $\rho$ is equal to between 0.1 and 3 mm; the second part $\rho$ is measured inward starting from the outermost end of the first part $\alpha$. These ranges will produce lower estimation errors and thus more realistic lenses.

More preferably, the first part $\alpha$ is equal to 0.7 times the diameter intersection diameter ID of the lens and the second part $\rho$ is equal to 0.5 mm.

The intersection diameter ID of the lens can be obtained using an intersection approach as the diameter in the intersection of the first and second parametric surfaces, which can be calculated for every lens.

The lens can be a crystalline lens or a prosthetic lens for replacing or supplementing a crystalline lens.

In some embodiments, the method further comprises correcting any optical and/or fan distortion produced by refraction by the cornea and anterior lens surfaces. This provides more accurate anterior and posterior surfaces lens measurements.

Once the full shape of the lens is estimated, the following geometrical parameters can be obtained: lens volume (VOL), equatorial diameter (DIA), equatorial plane position (EPP), surface area (SA) and also a parametric description of the laterals, e.g., values of the semi-axes from an ellipsoid fitting, curvature radius and asphericity from a conic fitting. In fact, the above methods preferably comprise obtaining one or more of these geometrical parameters.

In some embodiments, the accurate estimations of the EPP, VOL, DIA and SA provided by the disclosed method are used to predict where an intraocular lens (IOL) will be placed after cataract surgery (Estimated Lens Position, ELP), thereby being of great value when selecting the IOL power to be implanted in a patient as an input parameter in IOL power calculation formulas or ray tracing IOL power calculation methods.

The method of the present invention can be advantageously used to improve the estimation of the ELP and therefore the selection of an IOL based on ray tracing computation on patient-specific eye models or in typical power calculation formulas where the ELP (also called postoperative ACD) is needed (e.g., SRK/T formula). Advantageously, the selected IOL will provide better refractive, optical and visual outcomes.

The method of the present invention can be advantageously used to obtain a pre-operative estimation of the volume VOL of the crystalline lens, which is of high value in emerging treatments of presbyopia. In particular, knowledge of lens volume is critical in lens refilling techniques, in which the degree of filling of the capsular bag is essential to achieve the appropriate refraction and an adequate amplitude of accommodation. The lens volume VOL is also very important in the selection of several accommodative IOLs (A-IOLs), where prior knowledge of the DIA and VOL can enhance refractive predictability and be critical for the correct mechanism of action of the A-IOL.

Additionally, estimation of the shape of the entire lens can be useful to be employed in patient-dependent mathematical models and finite element modeling of the eye.

The optical imaging techniques used in the disclosed method can be one or more of Purkinje or Scheimpflug imaging techniques or Optical Coherence Tomography, OCT.

As indicated above, the disclosed method of estimating the full shape of a lens can be trained and validated using ex-vivo measurements. In this respect, the method further comprises previously finding a pair of values of the first and second parameters α, ρ that minimizes a merit or a cost function.

This pair of values of the first and second parameters {α, ρ} can be obtained by minimizing the mean squared error (or in general an error measurement) between the data of the actual lenses (ex-vivo lenses) and those of the lens as obtained with the present estimation method (estimated lenses).

Particularly, this pair of values of the first and second parameters {α, ρ} can be obtained by minimizing the mean estimation error over all the lenses of one or more of the following parameters of the lens: volume VOL, equatorial diameter DIA and/or equatorial plane position EPP using the ex-vivo measurements.

It is also possible to find that pair of values for α, ρ that minimizes the following equation:

$$J(\alpha,\rho) = VOLe + DIAe + EPPe,$$

where VOLe+DIAe+EPPe are the mean estimation errors between the estimated values of the geometrical parameters lens volume VOL, equatorial diameter DIA and equatorial plane position EPP, and their values as obtained from the ex-vivo measurements, normalized by their means and standard deviations.

Another aspect of the invention relates to a method of predicting an estimated lens position (ELP) of a lens to be implanted in an eye, which comprises using the method of estimating a full shape of a lens defined in the foregoing to obtain the estimated lens position (ELP).

That is, using the method of the invention previously defined, one or more parameters of the crystalline lens (e.g. VOL, DIA, SA and EPP) are obtained and one (or more) of them is used to estimate the position in which an intraocular lens implanted in an intracapsular cataract surgery procedure will be placed (the estimated lens position, ELP).

The estimated lens position (ELP) of the crystalline lens can be determined using the following formula:

$$ELP = a\frac{EPP}{THL} + b \cdot ACDpre$$

wherein 'a' and 'b' are coefficients, and ACDpre is the preoperative anterior chamber depth measured as the distance from the posterior cornea apex to the anterior lens apex and THL is the lens thickness.

The coefficient 'a' may range between 5-15 and the coefficient 'b' may range between 0-1; preferably, 'a' is 8.4966 and 'b' is 0.2499, which are the values that minimize the mean estimation error of the IOL position across lenses.

The estimated lens position (ELP) of the crystalline lens can also be determined using the following formula:

$$ELP = a \cdot THL\frac{SA}{VOL} + b \cdot THL$$

wherein 'a' and 'b' are coefficients, THL is the lens thickness, SA the surface area of the lens and VOL de volume of the lens.

In this case the coefficient 'a' ranges between 0 and 8 and the coefficient 'b' ranges between −2 and 2; preferably, 'a' is 1.72 and 'b' is −0.59.

Advantageously, this method of predicting the estimated the lens position (ELP) of the intraocular lens can be used to select an intraocular lens (IOL) to be implanted in an eye. Having an accurate estimation of the full shape of the crystalline lens results in a better selection of the IOL power of the lens to be implanted in a cataract surgery. The IOL power may be calculated based on ray tracing or on IOL power formulas.

The invention also relates to a device, particularly an optical imaging device such as an OCT, for estimating a full shape of a lens of an eye which comprises processing means for carrying out the method as defined in the foregoing.

A device for estimating a full shape of a lens of an eye is disclosed, the device comprising:
  means for receiving from measurements of the lens taken in-vivo by optical imaging techniques, the measurements comprising visible portions of the lens;
  processing means for defining non-visible portions of the lens parting from the in-vivo measurements and using a geometrical model of a lens previously built from ex-vivo measurements.

The invention also relates to an optical imaging device (such as an OCT), which comprises:
  means for receiving measurements of the lens taken by optical imaging techniques;
  processing means for carrying out one or more of the methods previously defined, and:
    estimate a full shape of a lens of an eye, by estimating one or more of the parameters of the lens; and/or,
    predict an estimated lens position (ELP) of a lens to be implanted in an eye; and/or,
    select an intraocular lens (IOL) to be implanted in an eye.

The different aspects and embodiments of the invention defined in the foregoing can be combined with one another, as long as they are compatible with each other.

Additional advantages and features of the invention will become apparent from the detail description that follows and will be particularly pointed out in the appended claims.

BRIEF DESCRIPTION OF THE DRAWINGS

To complete the description and in order to provide for a better understanding of the invention, a set of drawings is provided. Said drawings form an integral part of the description and illustrate an embodiment of the invention, which should not be interpreted as restricting the scope of the invention, but just as an example of how the invention can be carried out. The drawings comprise the following figures.

DESCRIPTION OF PREFERRED EMBODIMENTS

Figure 1:
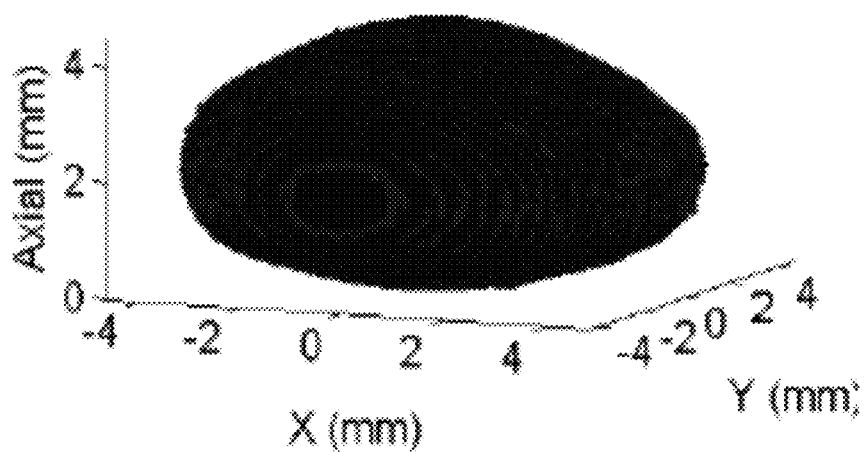
FIGS. 1 and 2 show 3-D plots of reconstructed volumes for a 38-year-old and a 67-year-old ex-vivo lenses, respectively.

The following description is not to be taken in a limiting sense but is given solely for the purpose of describing the broad principles of the invention. Next embodiments of the invention will be described by way of example, with reference to the above-mentioned drawings.

As will be shown in the following, in the present study the shape of the entire lens, and therefore VOL, DIA, SA and EPP, were estimated from in-vivo OCT measurements.

The measurements of the anterior surface, AL, and of the posterior surface, PL, of the crystalline lens were taken using OCT with fan and optical distortion correction algorithms, which has shown to be an excellent technique to image the anterior segment of the eye, due to its high-resolution and high-speed.

The present invention proposes a method for estimating a set of geometrical parameters of a crystalline lens as explained in detail herein below.

The method was trained and validated ex-vivo on twenty-seven human donor ex-vivo lenses (ranging from 19 to 71 years old), in which the information of the whole lens was available. In-vivo conditions were simulated for 3-D OCT volumes, assuming that only the information within a given pupil size (PS) was available. The entire lens geometry was estimated for a limited pupil using the method of the present invention, and the lens VOL, DIA and EPP compared to those computed from the whole lens. Optimal $\alpha$, $\rho$ were found by minimizing the error between the estimation from a limited pupil and the actual lens. Finally, these models were applied to in-vivo measurements in two young eyes during accommodation and in twelve eyes from 7 patients before cataract surgery.

The experiments were carried out with twenty-seven eyes from thirty human donors (ages ranging between 19 and 71 years), obtained from the Transplant Service Foundation (TSF) Eye Bank. Several parameters on this set of eyes (gradient refractive index (GRIN), thickness, curvature radius and topography) were known from previous reports (cf. "*Contribution of shape and gradient refractive index to the spherical aberration of isolated human lenses*" Birkenfeld J, de Castro A, Marcos S. Invest Ophthalmol Vis Sci 2014; 55:2599-2607). Eyes were shipped in sealed vials at 4° C., and wrapped in gauze soaked in preservation medium ([DMEM]/F-12, HEPES, no phenol red; GIBCO, Carlsbad, Calif., USA). The lens was carefully extracted from the eye and immersed in the same preservation medium at room temperature. During the measurements, the lens was placed on a ring in a DMEM-filled cuvette. The measurements took up two hours. Damaged, incomplete (information from the whole lens not being available) or excessively tilted lenses were identified from OCT images and excluded from the study. The handling and experimental protocols had been previously approved by the Institutional Review Boards of TSF and CSIC (Consejo Superior de Investigaciones Científicas). Methods for securing human tissue were in compliance with the Declaration of Helsinki.

For the in-vivo measurements: two eyes from two young subjects (33 and 32 years old; spherical errors 0D and −1.5D and cylinder <0.25 D) were measured during accommodation (relaxed and 6D stimulation). Twelve cataract eyes from seven subjects (79±5 years old) were measured prior to and after cataract surgery. All subjects involved in the present study signed a consent form approved by the Institutional Review Boards after they had been informed on the nature and possible consequences of the study, in accordance to the tenets of the Declaration of Helsinki.

The OCT images were acquired using a custom-developed spectral OCT system described in detail in "*Anterior segment imaging with Spectral OCT system using a high-speed CMOS camera*" Grulkowski I, Gora M, Szkulmowski M, et al. Opt Express 2009; 17:4842-4858. Briefly, the set-up is based on a fiber-optics Michelson interferometer configuration with a superluminiscent diode ($\lambda_0$=840 nm, $\Delta\lambda$=50 nm) as a light source and a spectrometer consisting of a volume diffraction grating, and a CMOS camera as a detector. The effective acquisition speed is 25000 A-Scans/s. The axial range is 7 mm in depth, resulting in a theoretical pixel resolution of 3.4 µm. The axial resolution is 6.9 µm.

For donor eyes, one 3-D volume was composed of 1168 A-scans, and 60 B-scans on a 12×12 mm lateral area, acquired in 4.5 seconds. The lens was first completely imaged with the anterior surface facing the OCT beam, and then was turned around a pre-determined axis and imaged again with the posterior surface facing the OCT beam.

For in-vivo measurements, one 3-D volume was composed of 300 A-scans, and 50 B-scans acquired in 0.6 seconds, showing a good balance between time acquisition and resolution. For accommodation measurements, a 11×11 mm lateral area was measured, and a Badal system mounted on a motorized stage (VXM-1, Velmex) was used for compensating defocus and for inducing accommodation. Five repeated measurements were collected in each accommodation state (0D and 6D) after inducing mydriasis with one drop of phenylephrine.

For cataract measurements, a 10×10 mm lateral area was measured, and measurements were conducted after inducing mydriasis with one drop of tropicamide. The specifications of the spectrometer and light source did not allow sufficient axial range to capture all anterior segment surfaces in a single acquisition. To solve that, three sets of 3-D images were captured sequentially at 5 seconds after blinking: (1)

cornea, (2) anterior lens and (3) posterior lens, shifting axially the plane of focus; all 3-D sets of data contained the iris.

Figure 2:
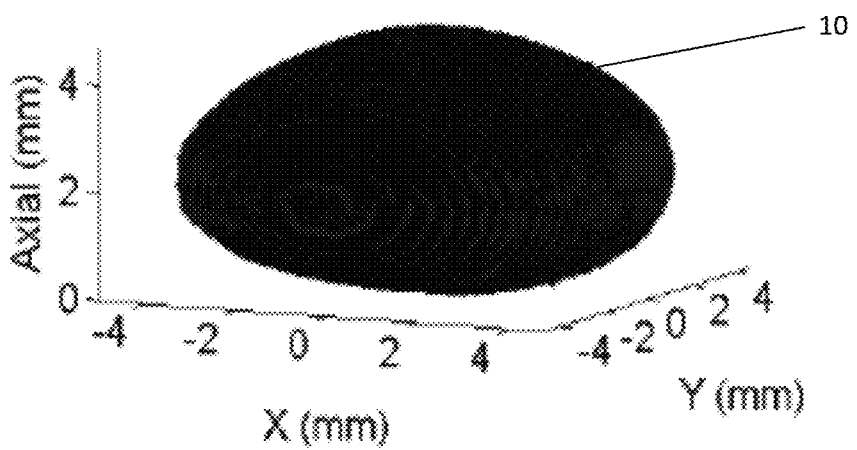

OCT Image Processing in Ex-Vivo Human Lenses:

The full volume of the lens was obtained by segmenting the first surface imaged in the following two conditions: the anterior surface of the lens facing the OCT beam ("anterior-up" images) and the posterior surface of the lens facing the OCT system ("posterior-up" images), and then registering both the anterior and posterior surfaces. B-scans were processed with semi-automatic surface segmentation algorithms and fan and optical distortion correction algorithms (group refractive index of the solution was taken as 1.345 at 825 nm). Registration was achieved by identifying, for both AL and PL, the lens cross-section parallel to XY-plane (i.e. normal to the optical axis of the lens, Z) exhibiting maximum area (i.e., the equatorial plane, where curvature changes from AL to PL) and by finding the 3-D displacement that maximized the intersection area between both (AL and PL) cross sectional planes. FIGS. 1 and 2 show reconstructed full lens volumes for a 38-year-old lens and a 67-year-old lens, respectively.

OCT Image Processing in In-Vivo Human Lenses:

Corneal and lens surfaces were automatically segmented for every B-scan, using previously described custom algorithms, such as the one described in "*OCT-based crystalline lens topography in accommodating eyes*", Pérez-Merino P, Velasco-Ocaña M, Martinez-Enriquez E, Marcos S., Biomed Opt Express 2015; 6:5039-5054. 3-D segmented corneal, AL and PL surfaces, were registered using the pupil center (obtained from the automatically identified iris volume in every of the three captured images in different depths) as a reference. Registered volumes were corrected for optical and fan distortion using 3-D ray tracing routines. The corneal group refractive index was taken as 1.385, the aqueous humor group refractive index as 1.345, and the crystalline lens refractive index was obtained from the age dependent average group refractive index expression derived by Uhlhorn et al ("*Refractive index measurement of the isolated crystalline lens using optical coherence tomography*". Vision Res 2008; 48:2732-2738).

Figure 3:
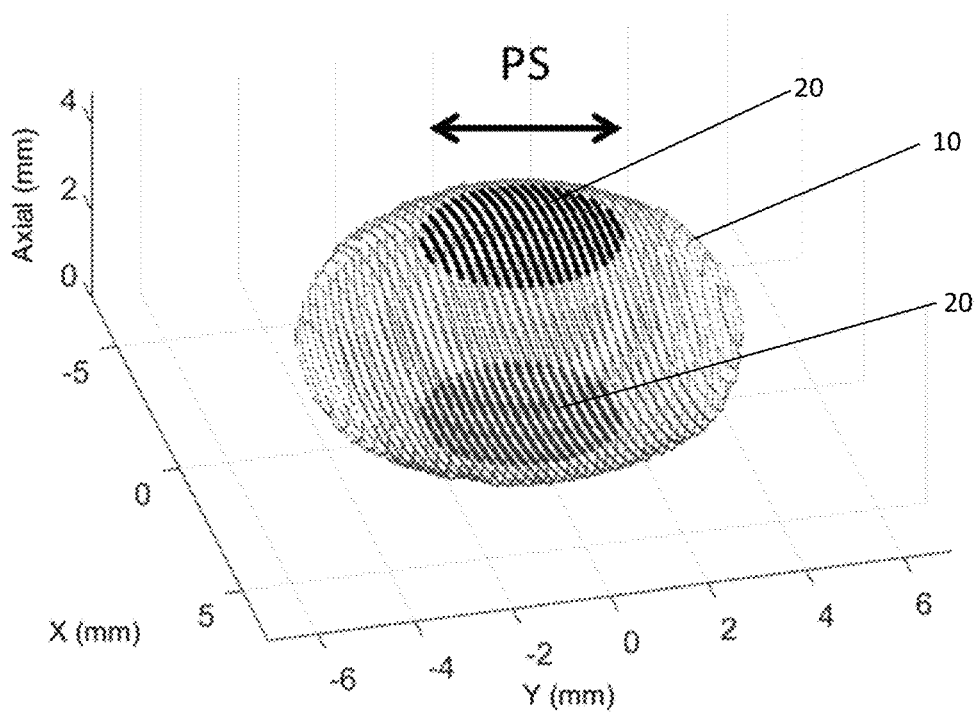
FIGS. 3-8 show, by means of 3-D plots, the different steps in the estimation of the full lens shape according to the present invention.
Figure 4:
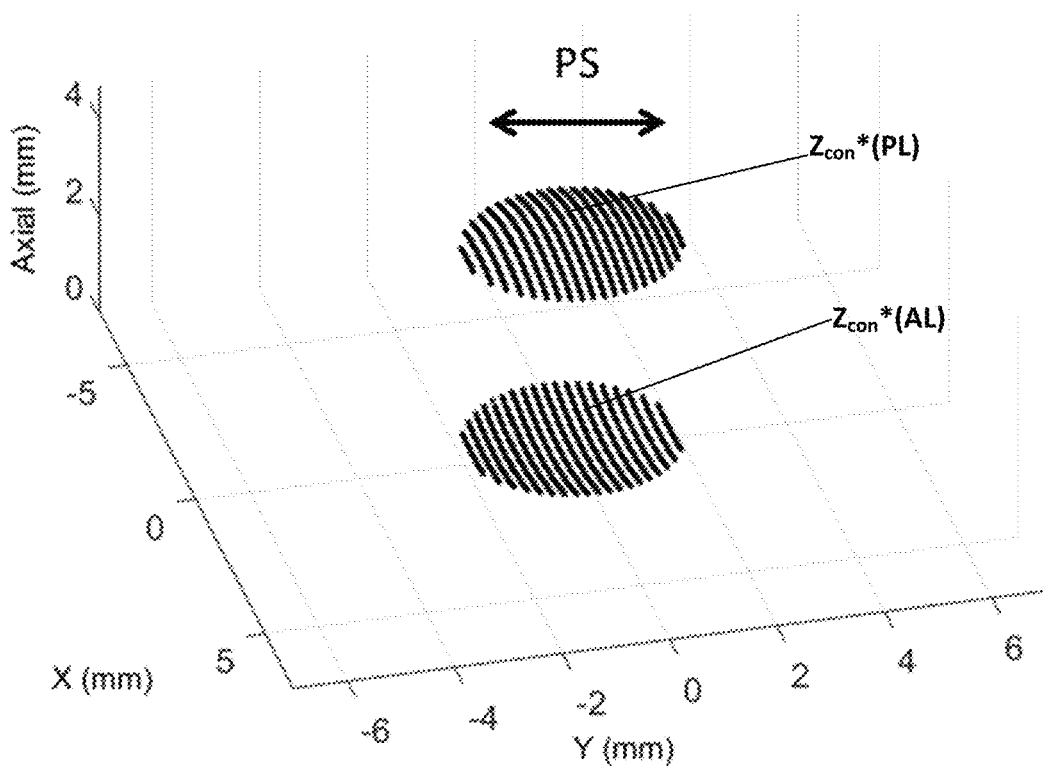
Figure 5:
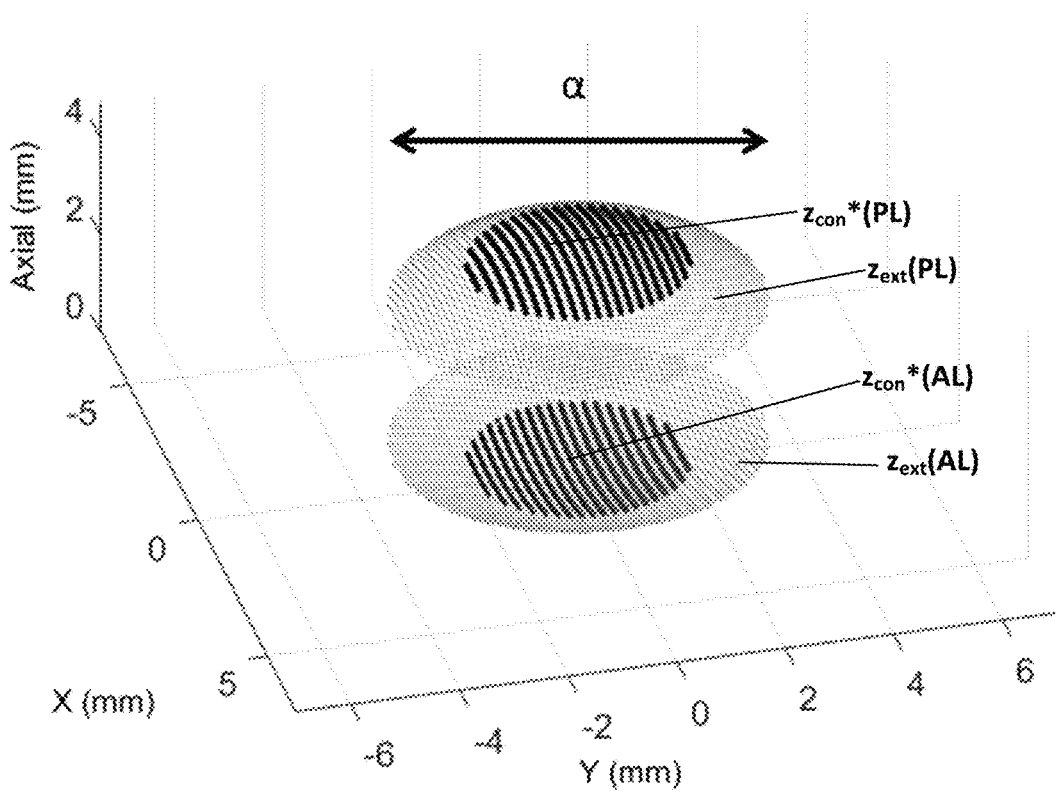
Figure 6:
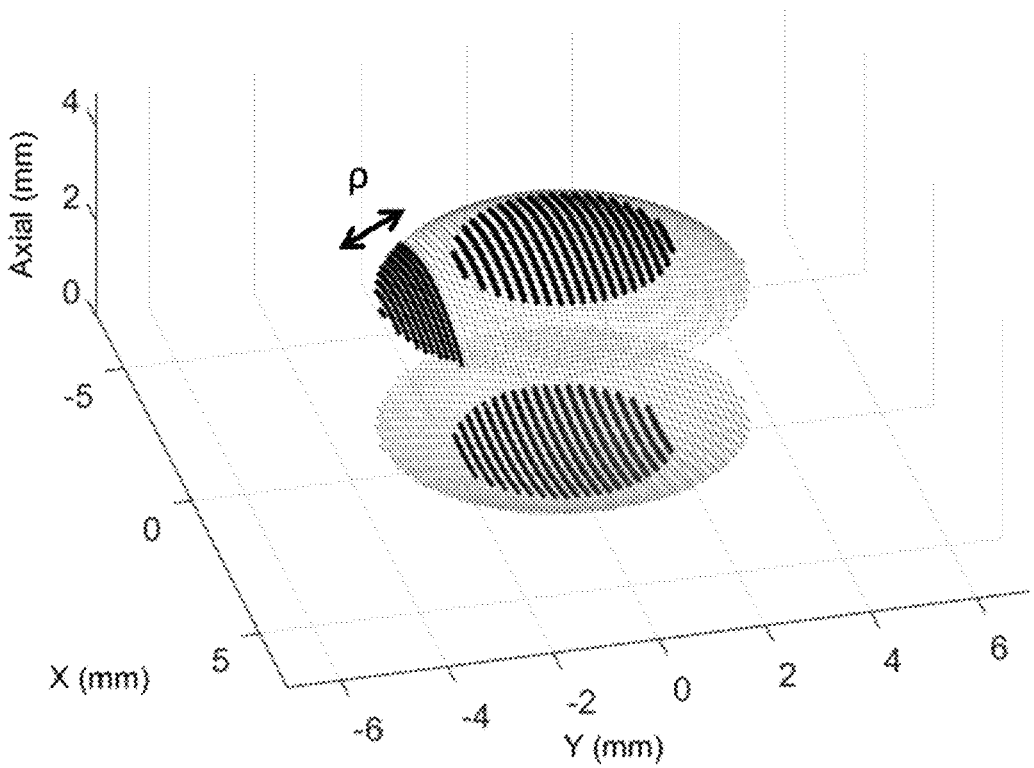

In a preferred embodiment of the method for estimating the lens shape according to the present invention, firstly, a lens model is constructed as follows:

From the ex-vivo full lens volume 10 (FIG. 3), it is assumed that only data 20 within a specific PS are available (shaded portion in FIG. 3), thereby simulating in-vivo conditions. From these PS data 20, the construction of the 3D model of the entire lens includes the following steps:

i) The anterior lens surface, AL, and the posterior lens surface, PL, are fitted (FIG. 4) within the portion delimited to the pupil size PS to parametric surfaces $z_{con}$-conicoids, biconicoids or ellipsoids-obeying the following equation:

$$z_{con} = \frac{\theta_1(x-x_0)^2 + \theta_2(y-y_0)^2}{1+\sqrt{1-(1+\theta_3)\theta_1^2(x-x_0)^2-(1+\theta_4)\theta_2^2(y-y_0)^2}} + z_0, \quad [1]$$

where x and y and are the coordinates of the sampling points within PS (i.e., so that $x^2+y^2 \leq (PS/2)^2$); and vector $\Theta$, $\theta=(\theta_1, \theta_2, \theta_3, \theta_4, x_0, y_0, z_0)$, contains the parameters of the surface. Note that $\theta_1=1/R_x$, $\theta_2=1/R_y$, $\theta_3=Q_x$, and $\theta_4=Q_y$ in biconicoids; $\theta_1=\theta_2=1/R$ and $\theta_3=\theta_4=Q$ in conicoids; and $\theta_1=c/a^2$, $\theta_2=c/b^2$, $\theta_3=a^2/c^2-1$, and $\theta_4=b^2/c^2-1$ in ellipsoids, with a, b and c being the semi-axes of the ellipsoid along the X, Y and Z axes. Terms ($x_o$, $y_o$, $z_o$) are the coordinates of the center of the parametric surface. The Z (axial) axis corresponds to the optical axis of the lens, as shown in the Figures. The fitting is performed using a non-linear multidimensional minimization algorithm.

ii) Using the parametric surfaces that best fit the anterior and posterior surfaces in the previous step $z_{con}*(AL)$, $z_{con}*(PL)$ (the * meaning that it is the best fitted surface), data within the non-available part of the central region are extrapolated to an extent given by parameter $\alpha$:

$$z_{ext} = z_{con}(\theta^*,x,y)$$

the extrapolated surfaces $z_{ext}(AL)$ and $z_{ext}(PL)$ being defined within $x^2+y^2 \leq (\alpha/2)^2$ as shown in FIG. 5.

iii) The equatorial region of the lens is then estimated, by fitting four parametric surfaces to the extrapolated data in the previous step. Specifically, a part ρ of the central region ($z_{ext}(AL)$ and $z_{ext}(PL)$ obtained from the previous step) measured inward starting from an outermost end of $z_{ext}(AL)$ and $z_{ext}(PL)$ was taken to fit every lens side, that is:

lens side #1: $\forall x, y \leq -\alpha/2+\rho$;

lens side #2: $x \geq \alpha/2-\rho, \forall y$;

lens side #3: $\forall x, y \geq \alpha/2-\rho$;

lens side #4: $x \leq -\alpha/2+\rho, \forall y$.

The fitting was performed using equation [1] interchanging the coordinate z with x (lens sides #2 and #4) or y (lens sides #1 and #3) in order to obtain a surface oriented along the desired axis. Again, a non-linear multidimensional minimization algorithm is used to fit the parametric surfaces (although other minimization algorithms are also possible).

Figure 7:
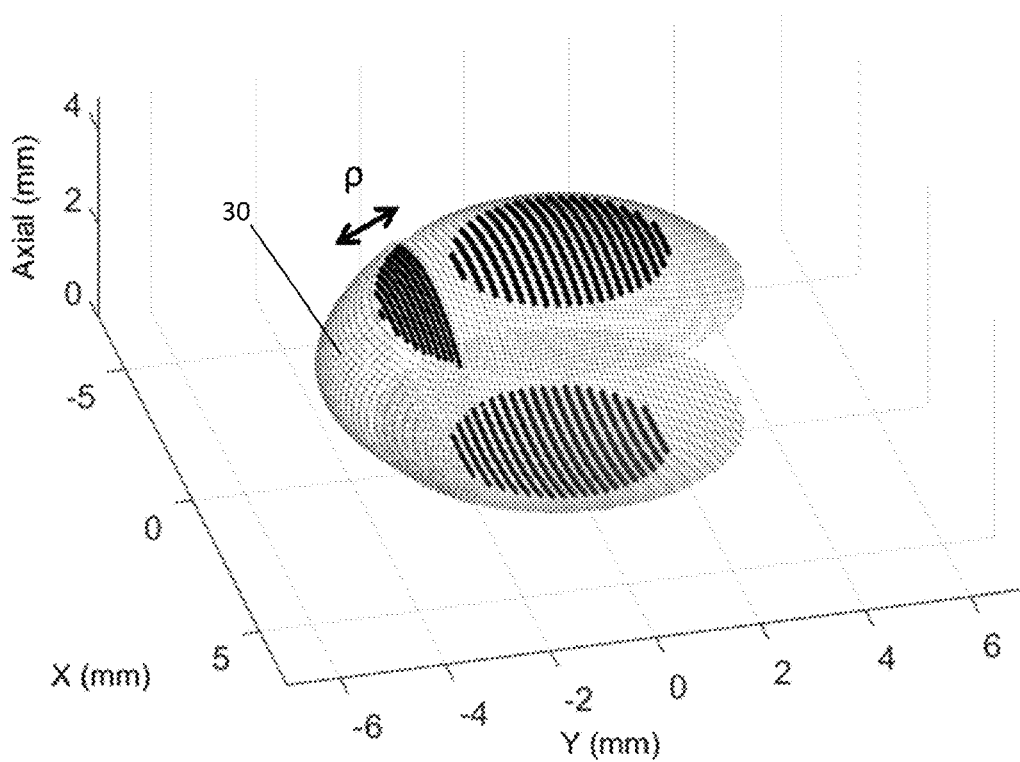
Figure 8:
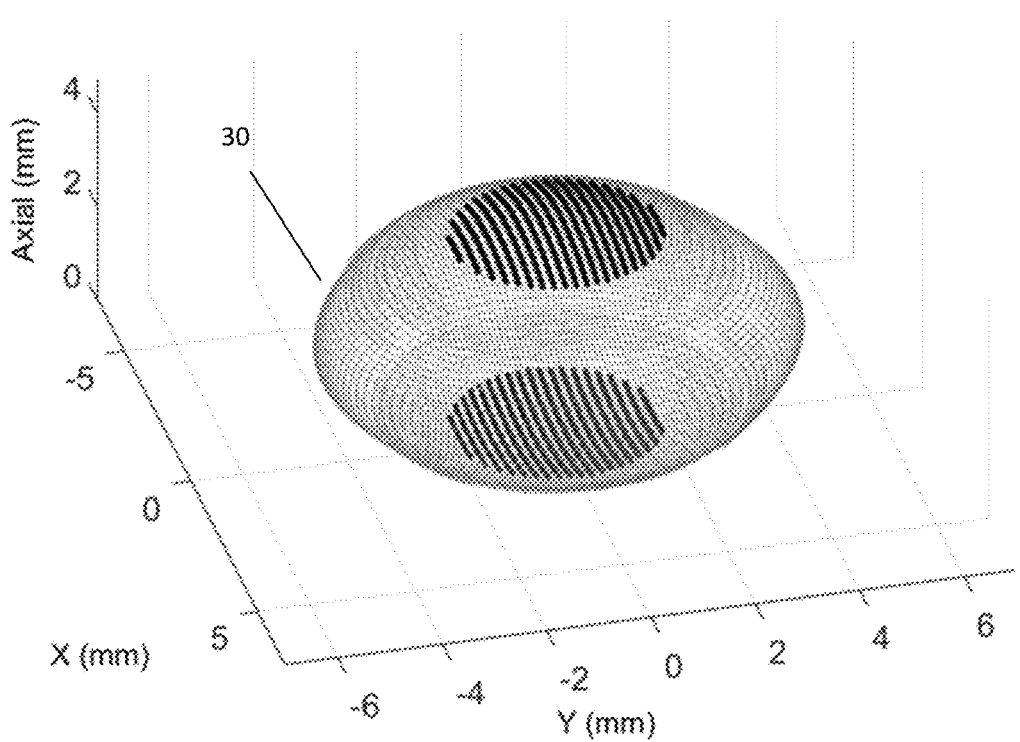

FIG. 7 shows one parametric surface (the lens side #1) 30 of the four parametric surfaces that define the equatorial regions of the lens. And FIG. 8 shows the final lens model with the four parametric surfaces obtained by fitting.

As previously defined, the parameter α indicates the extent of the central region of the lens, and the parameter ρ indicates the portion of the central region that should be taken into account to fit the equatorial regions of the lens. The reconstructed lens shape depends to a certain extent on the chosen values of α and ρ; large values of α will lead to an overestimation of DIA and VOL and vice-versa; and large values of ρ will lead to smoother lens equatorial regions but lower ability of the model to adapt to fast curvature changes. The optimal α depends on the lens geometry, in more particularly, on the diameter of the lens, DIA. It is also possible to calculate a as a function of the value of the derivative, or of the ratio thickness/ID (intersection diameter) for example. Since the lens diameter DIA is not known a priori, α is chosen as a proportion, PROP, of the diameter in the intersection, ID, of the parametric surfaces $Z_{con}*(AL)$, $Z_{con}*(PL)$ that best fit the anterior and posterior surfaces (from [1]), which can be calculated for every lens: α=PROP*ID.

Figure 9:
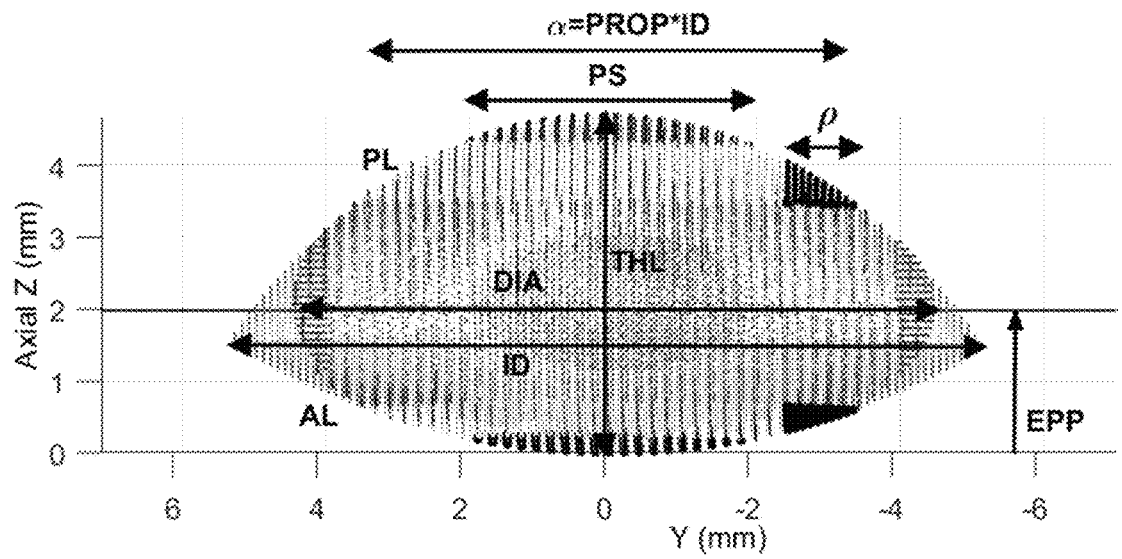
FIG. 9 shows a cross-section of a crystalline lens wherein ID, EPP and other parameters of interest are defined.

FIG. 9 shows a cross-section of a crystalline lens wherein ID, EPP and other parameters of interest are defined.

The training process consisted in finding the values of the parameters PROP and ρ which minimize the following equation:

$$\{PROP,\rho\}*= \arg \min_{\{PROP,\rho\}} J(PROP,\rho) \quad [3]$$

with $J(PROP,\rho) = VOLe + DIAe + EPPe$, \quad [4], where $VOL_e$, $DIA_e$ and $EPP_e$ are the mean estimation errors (the absolute value of the difference between their estimated values and their actual value) across the twenty-seven ex-vivo lenses, normalized by their means (μ) and standard deviations (σ) to be comparable:

$$J(\alpha,\rho)=((VOL-\mu VOL)/\sigma VOL)+((DIA-\mu DIA)/\sigma DIA)+((EPP-\mu EPP)/\sigma EPP)$$

The performance of the estimation model as previously defined was evaluated as follows:

Evaluation of the lens shape fitting surfaces: the optimal parametric surfaces (i.e. those minimizing the root mean square (RMS) of the residuals of the fitting in equation [1]) were evaluated for the fitting of the central and equatorial regions of the lens. Specifically, ellipsoids, conicoids and biconicoids were assessed. The central region of the lens within the PS (PS ranging between 4 and 5 mm) was better represented by biconicoids (RMS<40 μm) followed by ellipsoids (RMS<44 μm) and conicoids (RMS<50 μm). However, since biconicoids were less accurate in the extrapolation, ellipsoids were selected to fit the central region of the lens. VOL error was slightly lower using biconicoids to fit the equatorial regions of the lens (6.62 mm$^3$) than ellipsoids (6.92 mm$^3$), while DIA error was slightly higher with biconicoids (0.222 mm) than with ellipsoids (0.218 mm), and EPP error was approximately the same. Given the similar performance, and the lower number of parameters to be optimized, ellipsoids were also used to fit the equatorial regions of the lens.

Figure 10:
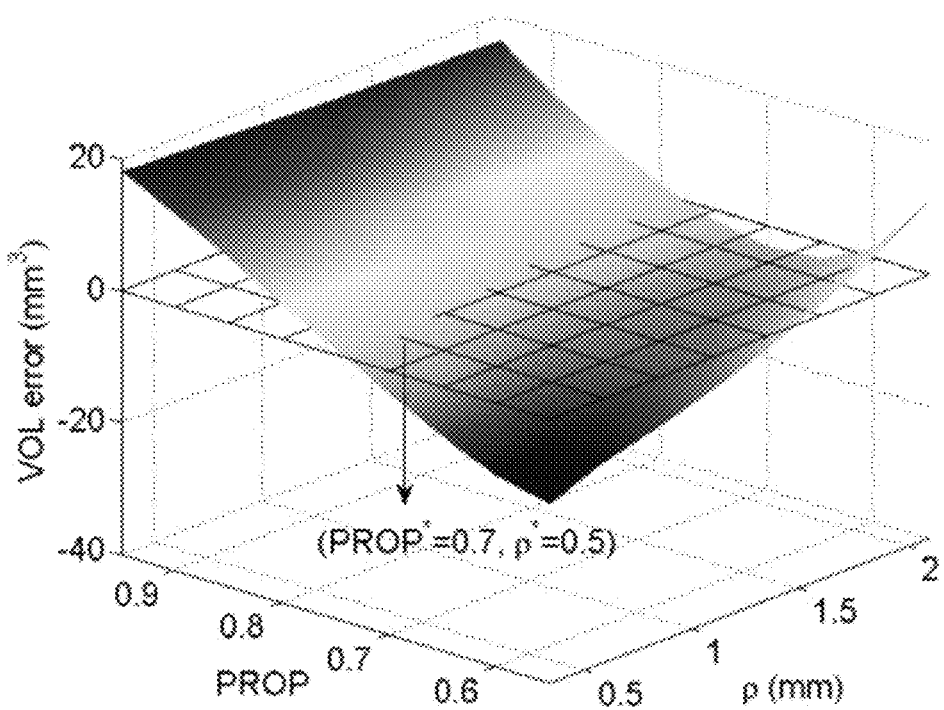
FIGS. 10 and 11 show graphs representing the optimal values of PROP and $\rho$.
Figure 11:
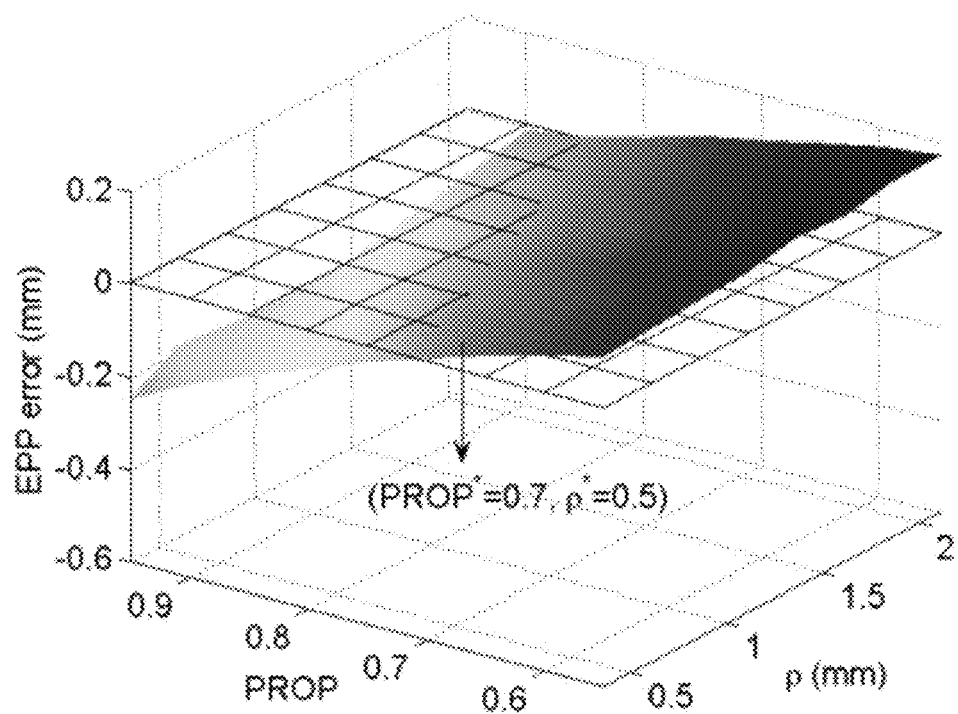

Evaluation of the estimation error as a function of the model parameters: as shown in FIGS. 10 and 11, the average estimation error of the lens volume VOL (FIG. 10), of the equatorial lens position EPP (FIG. 11) and of the lens diameter DIA (not shown) were analyzed as a function of pairs of the parameters PROP and ρ. For any ρ, as PROP tends to 1 the model approximates to an intersection model. When PROP and ρ are low, VOL and DIA are underestimated and EPP is overestimated.

FIGS. 10 and 11 show the optimal values of PROP and ρ obtained when minimizing equation [3].

The errors in the estimation of VOL, DIA and EPP were calculated for PS=4, 4.5 and 5 mm, using the optimal values of the parameters PROP and ρ. Crystalline lens VOL was estimated within 96% accuracy (mean errors across lenses: 9.30 7.49, 8.29 7.00 and 6.92 6.43 mm$^3$ for PS=4, 4.5 and 5 mm respectively). EPP was estimated with <45 μm (errors of 40±32, 39±34 and 36±32 μm) and errors in DIA were 0.26±0.22, 0.24±0.23 and 0.22±0.21 mm.

Comparison with Other Approaches

Figure 12:
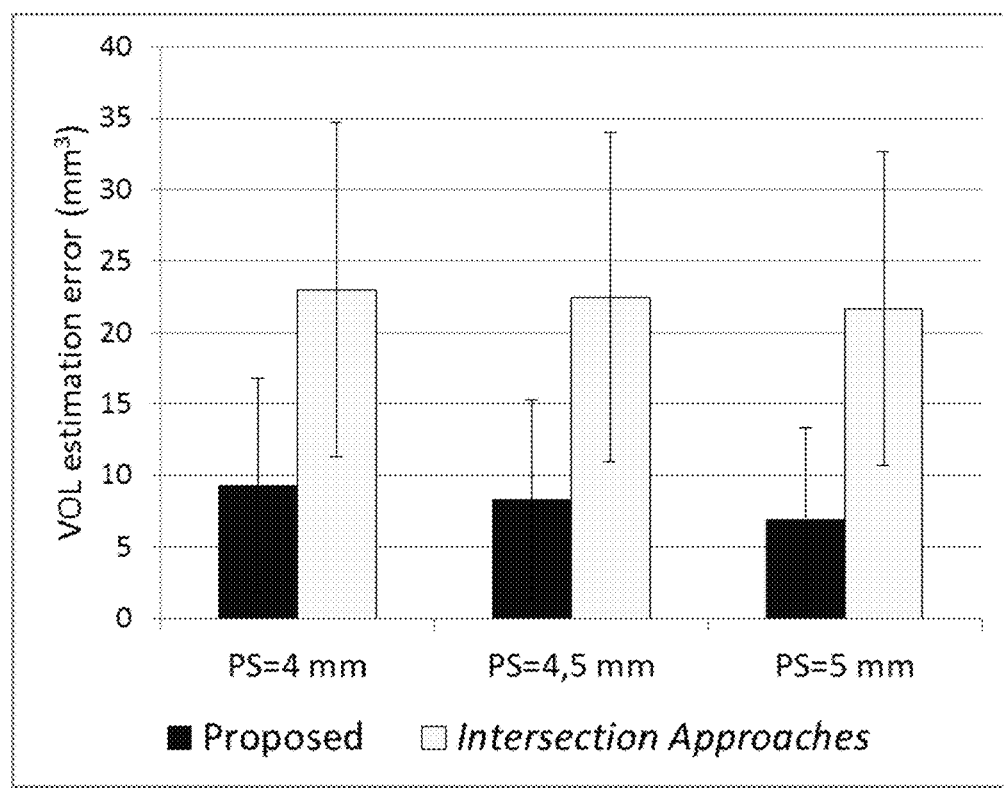
FIGS. 12 and 13 show the average VOL and DIA estimation errors with the proposed method and with an intersection approach.
Figure 13:
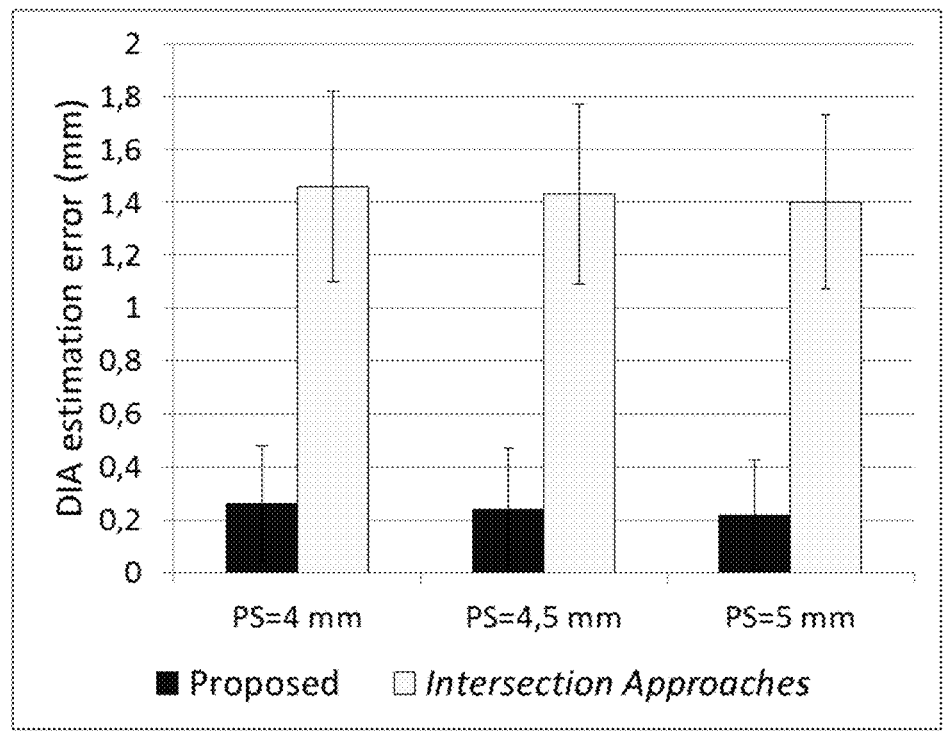

FIGS. 12 and 13 show the average VOL and DIA estimation errors in the data set of ex-vivo lenses estimated with the proposed method (left bars) and with an intersection approach (right bars).

Figure 14:
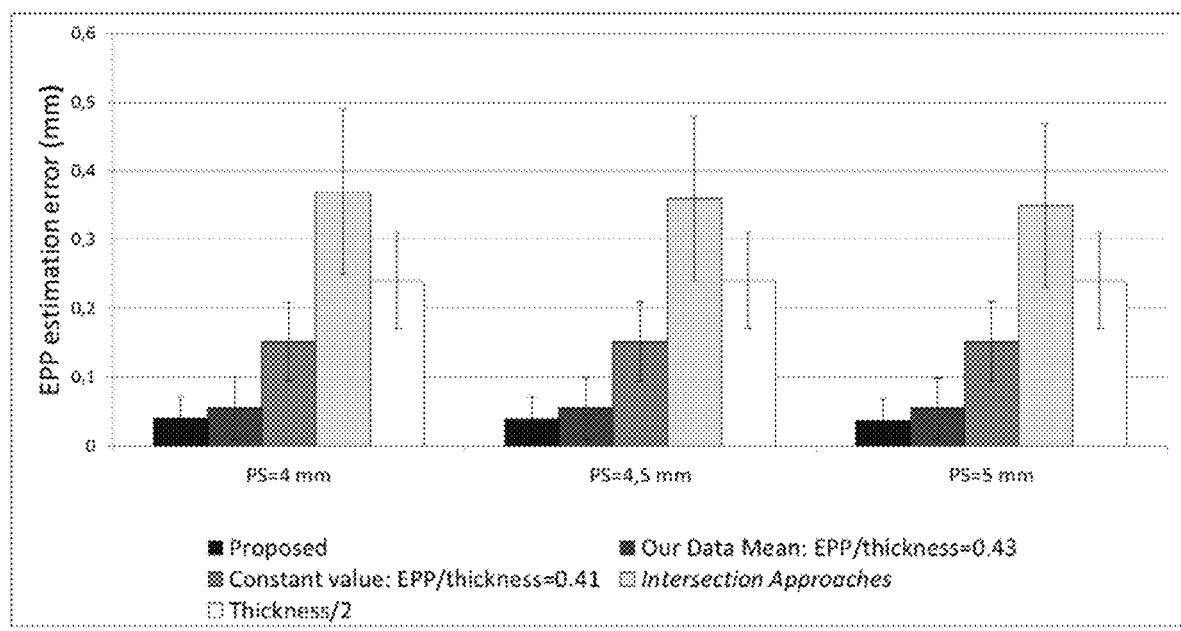
FIG. 14 shows the corresponding average EPP estimation error with the proposed method and with other approaches.

FIG. 14 shows the corresponding average EPP estimation error with the proposed method and with the mean value from the data set EPP/thickness=0.43, with an intersection approach, as well as with the constant value approach (EPP/thickness=0.41) and considering EPP=thickness/2.

Changes of the In-Vivo Crystalline Lens Shape with Accommodation

VOL, DIA and EPP were estimated in two young subjects during accommodation (for 0D and 6D, PS 5 mm). Lens VOL in-vivo remained almost constant with accommodation (from 180.0 (0D) to 180.4 (6D) mm$^3$ in the first subject S#1 and from 156.1 to 156.2 mm3 in the second subject S#2), DIA decreased from 9.5 to 9.36 mm in S#1 and from 8.6 to 8.46 mm in S#2, and EPP increased (backward shift) from 1.72 to 1.82 mm in S#1 and from 2.02 to 2.19 mm in S#2.

Crystalline Lens VOL, DIA, SA and EPP in Cataract Eyes

VOL, DIA, EPP an SA were estimated from the preoperative measurements in the twelve cataract eyes. The average estimated lens values across eyes were VOL=208±29 mm$^3$, DIA=9.33±0.30 mm, SA=184±14 mm$^2$ and EPP=2.14±0.25 mm.

Accuracy of the Method

Crystalline lens VOL was estimated within 96% accuracy. EPP was estimated with <45 μm. Errors in DIA were less than 0.26 mm. The proposed method shows an improved performance in comparison with state of the art methods, leading to VOL and DIA estimation errors around 3 and 6 times lower, respectively.

Comparison with Earlier Work

In the accommodative eyes, it was found that VOL remained constant with accommodation and that DIA increased and EPP backward shifted, which is consistent with previously reported results. Besides differences in the imaging modality and the lens parametric modeling, most previous studies are based on cross-sectional images of the lens. Recent studies have revealed the relevance of lens surface astigmatism and errors associated to the assumption of lens rotational symmetry.

The above results show that it is possible to obtain an accurate estimation of human crystalline lens volume, shape and equatorial lens position, as demonstrated from ex-vivo measurements, where entire lens images are available.

As previously indicated, fan and optical distortions corrections are very important to obtain accurate quantitative data and therefore accurate estimations of the entirely lens shape (VOL, DIA, EPP). If distortions are not corrected AL and PL curvature radii are highly overestimated. Lens parameter estimates were compared with and without fan and optical distortion corrections in lenses in-vivo and found that not correcting for these distortions resulted in an overestimation of VOL by 25%, of DIA by 15%, and an anterior shift of EPP by 8%.

It was also found that the ratio EPP/thickness is subject dependent (ranging from 0.40 to 0.47, 0.43 on average), in agreement with previous reports, and unlike assumptions using a constant value (0.41).

The Influence of GRIN

The ex-vivo lens 3-D volumes were constructed from two sets of OCT measurements obtained with the anterior lens surface up and posterior surface up, not affected by the GRIN. However, in-vivo OCT measurements of the posterior lens surface were obtained through the anterior surface, assuming a homogeneous refractive index in the optical distortion correction. Earlier work showed that an uncertainty of ±0.01 in the refractive index produces an uncertainty on the order of ±1% in the lens VOL and suggested that ignoring the GRIN introduced a negligible error. Also, in a previous work it was shown that GRIN did not affect significantly the estimation of lens radii of curvature, although posterior lens asphericity estimates may in fact be affected by neglecting the presence of GRIN. Recent estimates of GRIN distribution profiles in human lenses can be used to further refine the estimates.

Extrapolation of Ex-Vivo Lens Model Construction for In-Vivo Applications

Lens models have been trained with isolated ex-vivo lenses with a wide range of geometries. A large number of our lens sample correspond to nearly presbyopic or presbyopic eyes, where one expects minimal changes with accommodation and thus ex-vivo and in-vivo lenses are expected to have approximately the same shape. In addition, the fact that we did not find a dependency on the optimal parameters (PROP* and ρ*) across lenses of different ages and that VOL was estimated to be constant with accommodation in vivo, suggests that the method was not biased from using ex-vivo lenses in the training process.

Estimated Lens Position in Cataract Surgery

Twelve eyes from 7 patients (79±5 years old) were measured before (inducing mydriasis with one drop of tropicamide) and after cataract surgery. The intraocular lens implanted was the Carl Zeiss CT Asphina409M IOL in all the patients, with IOL power calculated using the SRK/T formula. The surgery was performed using phacoemulsification through a 2-mm incision.

ELP was estimated using the EPP calculated from the full shape of the lens obtained with the method of estimating the full shape of the lens present invention. Specifically, the ELP was estimated using a proposed formula that linearly relates the ELP with the EPP/THL ratio and the ACD preoperative:

$$ELP = 8.4966 \frac{EPP}{THL} + 0.2499 \, ACDpre,$$

where THL is the measured lens thickness and ACDpre is preoperative anterior chamber depth, measured as the distance between posterior cornea apex and anterior lens apex.

This formula was obtained by linear regression using the available data.

The ELP was also obtained with methods in the state of the art for lens estimation, namely:

Using the C constant for the corresponding lens (Asphina 409) proposed by Olsen and Hoffmann ("*C constant: New concept for ray tracing-assisted intraocular lens power calculation*", Olsen T, Hoffmann P, Journal of Cataract & Refractive Surgery 2014; 40:764-773): 0.39

Using the C constant proposed by Olsen and Hoffmann optimized with our data: 0.397

Using the ELP from the SRK/T formula (also called postoperative ACD).

Using the intersection approach.

Figure 15:
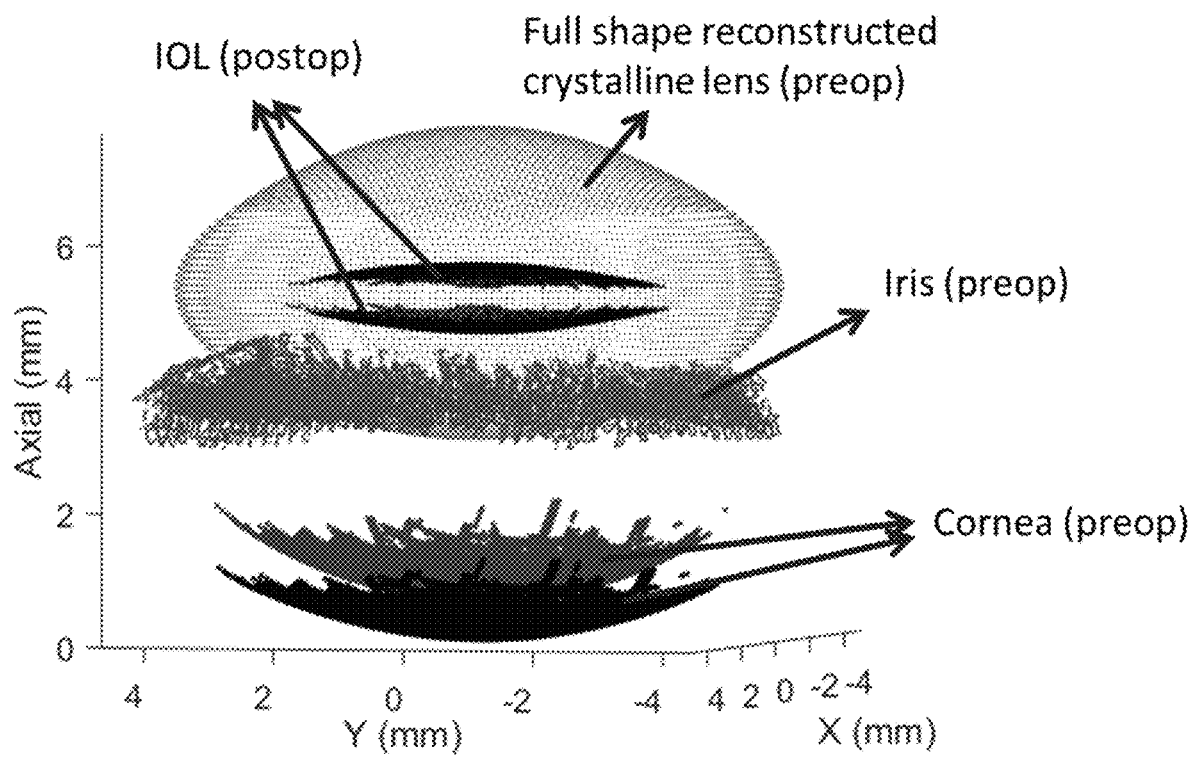
FIG. 15 shows the anterior segment 3-D preoperative model and postoperative IOL superimposed.

To evaluate the accuracy of the estimations, postoperative OCT measurements (after IOL implantation), where the IOL can be clearly seen and measured, were used to calculate the actual position of the IOL (LP) after surgery. FIG. 15 shows the preoperative 3-D model constructed (including the full shape crystalline lens) and the postoperative IOL superimposed.

Figure 16:
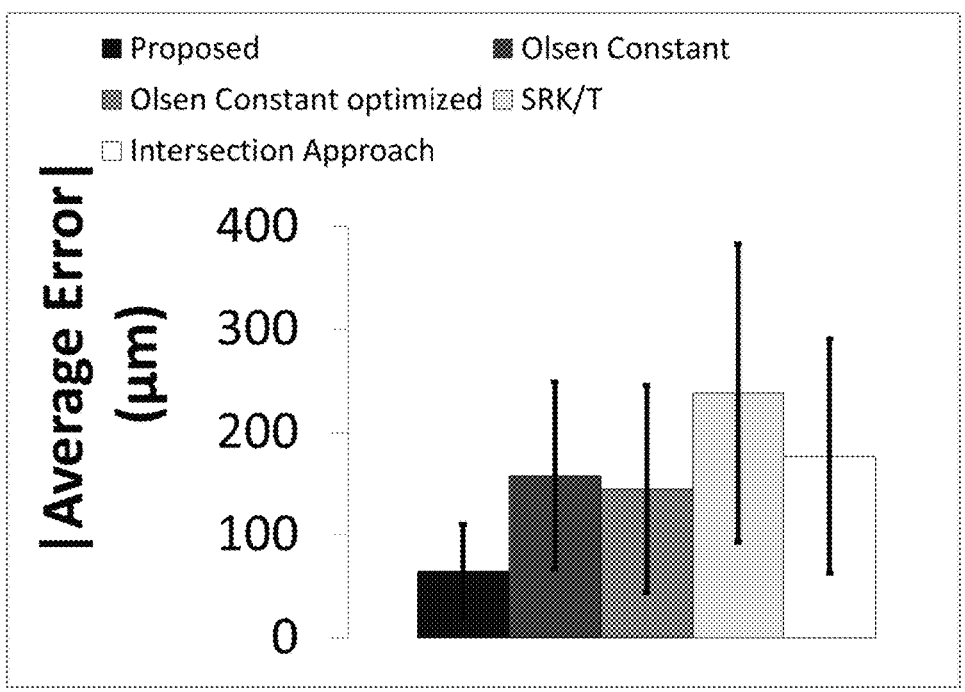
FIG. 16 shows the ELP estimation error with the proposed method and with other approaches, mean±standard deviation across subjects.
Figure 17:
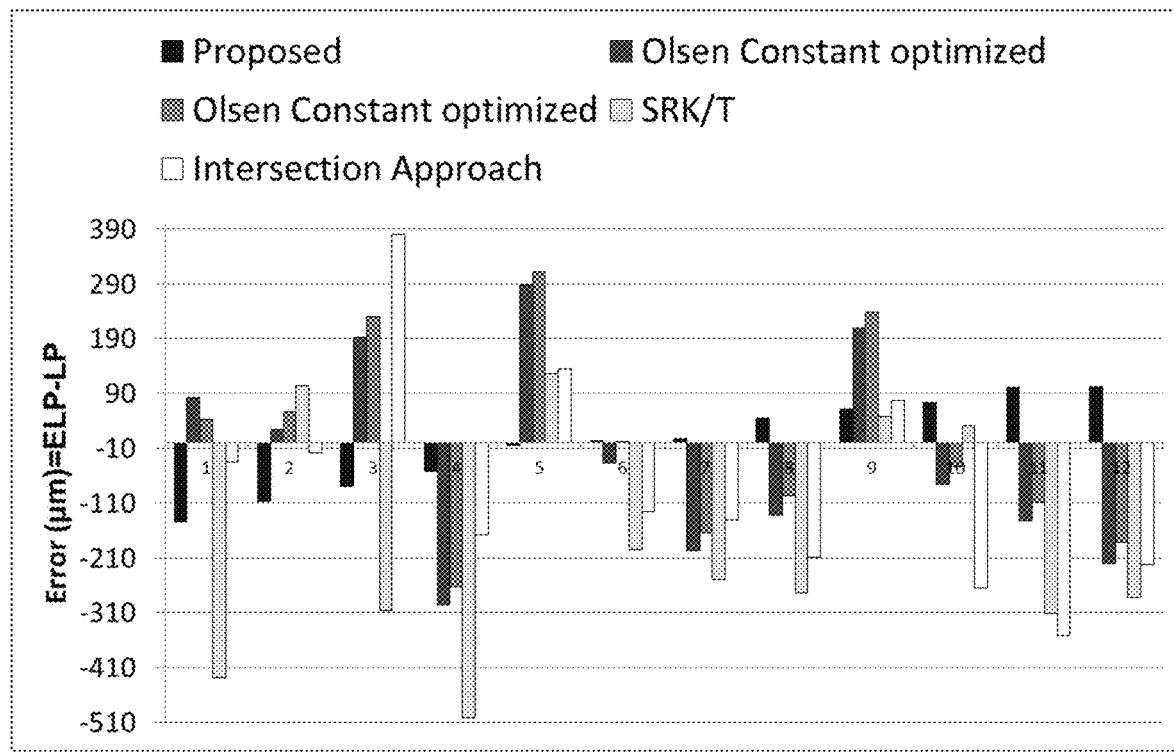
FIG. 17 shows the ELP estimation error with the proposed method and with other approaches for every eye.

The error was calculated as the difference between the prediction using the different methods mentioned above and the actual lens position (LP, obtained from the postoperative measurements), i.e., error=estimation−LP. The mean error and standard deviation of the absolute value of the error over the 12 eyes were obtained for the different methods. The mean error was 64.9 μm±44.9 with the proposed estimation, 158 μm±91 with the C constant by Olsen, 145 μm±101 with the C constant optimized with our data set, 238 μm±145 with the SRK/T estimation, and 177 μm±114 with the intersection approach. FIG. 16 shows the average±standard deviation of the estimation error across eyes, and FIG. 17 shows the estimation error for every eye, for the compared estimation methods.

Note that the estimation error with the proposed invention was more than 2 times less than using the C constant by Olsen (even if the constant was optimized with our data set) and around 3 times less than using the SRK or intersections approaches. Furthermore, the deviation in the estimation error among patients was much lower with the proposed formula, which stresses the importance of individual-full shape of the lens measurements for proper estimation of the estimated lens position.

To evaluate the improvements in terms of postoperative refractive error, the estimation of the IOL position (ELP) using the proposed formula was used in the SRK/T IOL power calculation formula, leading to the IOL power for emmetropia using the proposed ELP. Obtained values were compared with the IOL power directly suggested using the SRK/T (and thus its estimation of ELP (postoperative ACD)), and postoperative refraction improvements were estimated using the measured objective postoperative refractive error with an auto refractometer.

Figure 18:
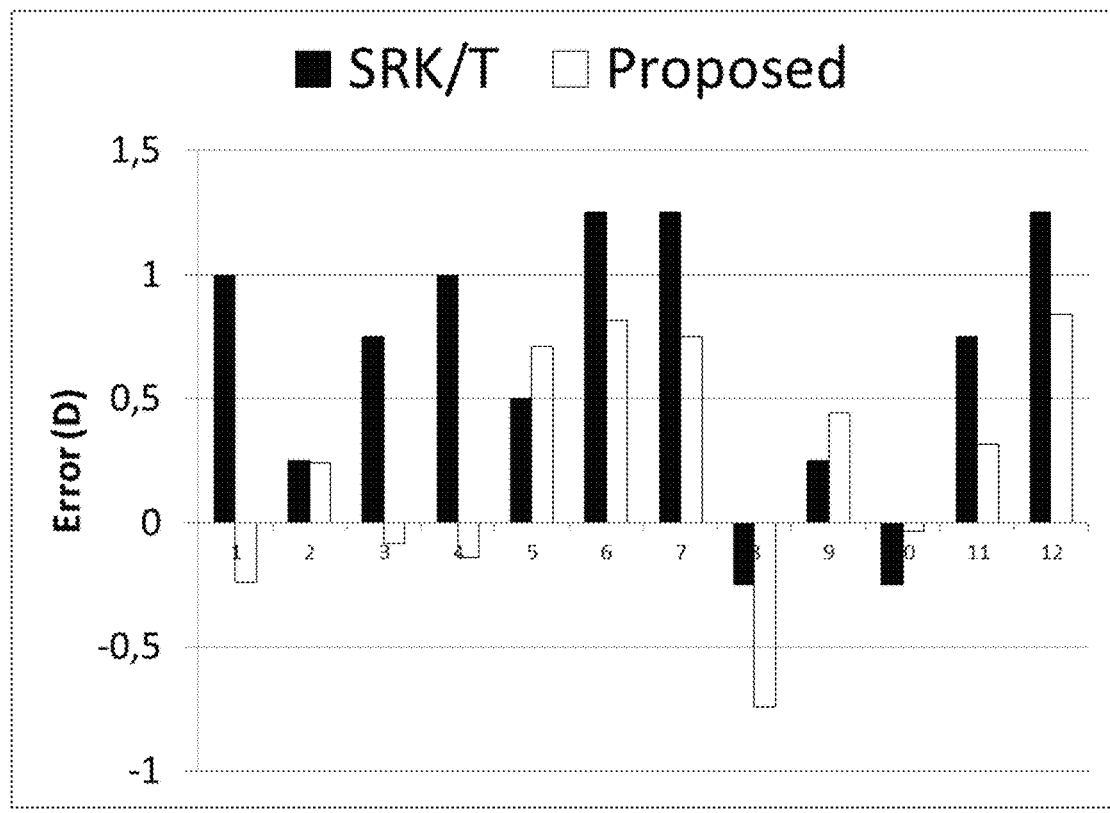
FIG. 18 shows the postoperative refractive error with the proposed method and with the SRK/T for every eye.

FIG. 18 shows the postoperative refractive error for the proposed method and the SRK/T.

If the IOL power is chosen using the proposed invention, patients will be 0.29 D on average closer to emmetropia than using the standard ELP estimation applied in the SRK/T formula, obtaining improvements of 0.86 D in one of the subjects (the refractive error is reduced 0.86 D), improvements greater than 0.5 D in 4 subjects, and greater than 0.4 D in 7 subjects.

These results show an improvement of IOL power selection using the proposed ELP approach over approaches based on limited anatomical information (e.g., the Radius of curvature of anterior cornea and the axial length of the eye in the SRK/T ELP) further improving previous proposals which included for the first time lens thickness data. Thus, knowledge of the full lens shape, and in particular EPP, is very valuable to estimate ELP.

The results have been obtained using the proposed ELP in the SRK/T formula for IOL power selection, which assumes some simplifications (e.g., the posterior cornea radius of curvature is not taken into account in the formula). Further improvements will be obtained using full OCT-based quantification of the anterior segment of the eye for every patient prior to cataract surgery (anterior and posterior corneal topography, 3-D biometry and the proposed ELP based on the full shape of the crystalline lens) and ray tracing based IOL power selection.

Alternatively, another relationship that was found between the estimated lens position ELP and one or more of the geometrical parameters of the lens was:

$$ELP = 1.72 THL \frac{SA}{VOL} - 0.59 THL$$

In summary, quantitative OCT with dedicated image processing algorithms allows accurate estimation of human crystalline lens volume, shape and equatorial lens position, as demonstrated from ex-vivo measurements, where entire lens images are available. Patient-specific eye models that include the information on lens volume and equatorial lens position are critical for better IOL selection (based on ray tracing or in traditional formulas), and will help in presbyopia-correcting paradigms including crystalline lens refilling and accommodative IOLs.

In this text, the term "comprises" and its derivations (such as "comprising", etc.) should not be understood in an excluding sense, that is, these terms should not be interpreted as excluding the possibility that what is described and defined may include further elements, steps, etc.

On the other hand, the invention is obviously not limited to the specific embodiment(s) described herein, but also encompasses any variations that may be considered by any person skilled in the art (for example, as regards the choice of materials, dimensions, components, configuration, etc.), within the general scope of the invention as defined in the claims.

The invention claimed is:

1. A method of estimating a full shape of a crystalline lens for an eye from measurements of the crystalline lens taken in-vivo by optical imaging techniques, the measurements comprising visible portions of the crystalline lens, the method comprising:
   defining non-visible portions of the crystalline lens parting from the in-vivo measurements and using a geometrical model of a crystalline lens previously built and trained from ex-vivo measurements;
   fitting the in-vivo measurements which comprise visible portions of the crystalline lens, to a first parametric surface corresponding to an anterior surface (AL) of the crystalline lens and to a second parametric surface corresponding to a posterior surface (PL) of the crystalline lens;
   defining the non-visible portions of the crystalline lens by:
   extrapolating the first and second parametric surfaces to an extent given by a first parameter ($\alpha$) to define a central region of the crystalline lens, that includes the visible portions and an extrapolated non-visible portion;
   using data from a part of the central region of the crystalline lens to define an equatorial region of the lens by at least a third parametric surface, the part being given by a second parameter ($\rho$);
   wherein the first and second parameters ($\alpha,\rho$) are given by the geometrical model built and trained from the ex-vivo measurements.

2. The method according to claim 1, wherein the step of using data from the part of the central region of the lens comprises fitting such data to the at least third parametric surface.

3. The method according to claim 1, wherein the step of using data from the part of the central region of the crystalline lens comprises imposing continuity and differentiability conditions between the extrapolated first and second parametric surfaces and the at least third parametric surface.

4. The method according to claim 1, wherein the extent given by the first parameter ($\alpha$) is equal to 0.55-0.95 times an intersection diameter (ID) of the lens and the second parameter ($\rho$) is equal to 0.1-3 mm.

5. The method according to claim 1, wherein the first parameter ($\alpha$) is equal to 0.7 times an intersection diameter (ID) of the crystalline lens and the second parameter ($\rho$) is equal to 0.5 mm.

6. The method according to claim 1 wherein the in-vivo measurements are previously corrected using any fan and/or optical distortion correction method.

7. The method according to claim 1 further comprising previously finding a pair of values of the first and second parameters ($\alpha,\rho$) that minimizes a merit function.

8. The method according to claim 1 further comprising previously finding a pair of values of the first and second parameters ($\alpha,\rho$) that minimizes the following equation:

$$J(\alpha,\rho) = VOLe + DIAe + EPPe$$

where VOLe+DIAe+EPPe, are the mean estimation errors between the estimated values of geometrical parameters: lens volume (VOL), equatorial diameter (DIA) and equatorial plane position (EPP) and their values as obtained from the ex-vivo measurements, normalized by their means and standard deviations.

9. The method according to claim 1 further comprising previously finding a pair of values of the first and second parameters ($\alpha,\rho$) that minimize the mean estimation error over the lenses of the following parameters of the lens: volume (VOL), equatorial diameter (DIA) and/or equatorial plane position (EPP) using the ex-vivo measurements.

10. A method of predicting an estimated lens position (ELP) of an intraocular lens to be implanted in an eye, using the method of claim 1 to estimate the full shape of a crystalline lens; and obtaining the estimated lens position (ELP) from the full shape of the crystalline lens or from one or more of the following parameters of the lens: volume (VOL), equatorial diameter (DIA), surface area (SA) and equatorial plane position (EPP), or a combination thereof.

11. The method according to claim 10, wherein the estimated lens position (ELP) of the intraocular lens to be implanted in an eye is determined using the following formula:

$$ELP = a\frac{EPP}{THL} + bACDpre$$

wherein a and b are coefficients, ACDpre is the preoperative anterior chamber depth measured as the distance from the posterior cornea apex to the anterior crystalline lens apex and THL is the crystalline lens thickness.

12. The method according to claim 11, wherein the coefficient 'a' ranges between 5-15 and the coefficient 'b' ranges between 0-1.

13. The method according to claim 10, wherein the estimated lens position (ELP) of the crystalline lens is determined using the following formula:

$$ELP = aTHL\frac{SA}{VOL} + bTHL$$

wherein a and b are coefficients, THL is the crystalline lens thickness, SA is the surface area of the crystalline lens and VOL is the volume of the crystalline lens.

14. The method according to claim 13, wherein the coefficient 'a' ranges between 0 and 8 and the coefficient 'b' ranges between −2 and 2.

15. A method of selecting an intraocular lens (IOL) to be implanted in an eye, which comprises using the method of claim 10 to calculate the estimated lens position (ELP) of the intraocular lens.

16. An optical imaging device, which contains processing means for carrying out the method of claim 1.

17. A method of predicting an estimated lens position (ELP) of an intraocular lens to be implanted in an eye, which comprises using the method of claim 1 to estimate the full shape of a crystalline lens;
   wherein the estimated lens position (ELP) is determined using the following formula:

$$ELP = a\frac{EPP}{THL} + bACDpre$$

wherein a and b are coefficients, ACDpre is the preoperative anterior chamber depth measured as the distance from the posterior cornea apex to the anterior crystalline lens apex and THL is the crystalline lens thickness.

18. A method of estimating a full shape of a crystalline lens of an eye from measurements of the crystalline lens taken in-vivo by optical imaging techniques, the method comprising:

fitting the in-vivo measurements to a first parametric surface corresponding to an anterior surface (AL) of the crystalline lens and to a second parametric surface corresponding to a posterior surface (PL) of the crystalline lens;

extrapolating the first and second parametric surfaces to an extent given by a first parameter ($\alpha$) to define a central region of the crystalline lens, that includes the visible portions and the non-visible extrapolated portion;

using data from a part of the defined central region of the crystalline lens to define an equatorial region of the crystalline lens by obtaining at least a third parametric surface that adapts to such data, the part being given by a second parameter ($\rho$).

19. The method according to claim 3 further comprising taking in-vivo measurements of the anterior surface (AL) and the posterior surface (PL) of the crystalline lens with an optical imaging technique.

* * * * *